United States Patent [19]

Koppes et al.

[11] Patent Number: 5,268,429
[45] Date of Patent: Dec. 7, 1993

[54] POLYMER PROCESS

[75] Inventors: Margaretha J. C. M. Koppes; Johannes A. Van Doorn; Judith J. B. Walhof, all of Amsterdam, Netherlands

[73] Assignee: Shell Oil Company, Houston, Tex.

[21] Appl. No.: 889,346

[22] Filed: May 28, 1992

[30] Foreign Application Priority Data

Jun. 3, 1991 [GB] United Kingdom ............... 9111872

[51] Int. Cl.$^5$ .................. C08F 8/30; C08F 261/06; C08K 5/53
[52] U.S. Cl. .................. 525/255; 525/314; 525/332.9; 525/340
[58] Field of Search ............ 525/314, 255, 332.9, 525/340

[56] References Cited

U.S. PATENT DOCUMENTS

| | | | |
|---|---|---|---|
| 2,726,226 | 12/1955 | Werkheiser | 525/255 |
| 3,147,313 | 9/1964 | Hsieh | 260/837 |
| 3,278,464 | 10/1966 | Boyer | 525/340 |
| 3,341,629 | 9/1967 | Larrison | 525/340 |
| 3,419,524 | 12/1968 | Larrison | 525/240 |
| 3,676,393 | 7/1972 | Piirma | 524/132 |
| 3,697,620 | 10/1972 | Ermidis | 525/255 |
| 3,778,490 | 12/1973 | Hsieh | 260/880 B |
| 3,803,266 | 4/1974 | Kable et al. | 525/340 |
| 3,898,209 | 8/1975 | Watson et al. | 528/481 |
| 4,233,207 | 11/1980 | Spivack | 524/134 |
| 4,248,984 | 2/1981 | Bi et al. | 525/314 |
| 4,369,260 | 1/1983 | Younes | 525/340 |
| 4,474,914 | 10/1984 | Spivack | 524/126 |
| 4,485,833 | 12/1984 | Uraneck et al. | 525/340 |
| 4,537,932 | 8/1985 | Uraneck et al. | 525/332.9 |
| 4,581,415 | 4/1986 | Boyle, Jr. et al. | 525/332.9 |

FOREIGN PATENT DOCUMENTS

| | | |
|---|---|---|
| 135962A | 4/1985 | European Pat. Off. . |
| 192154A | 8/1986 | European Pat. Off. . |
| 2367098 | 10/1976 | France . |
| 1484187 | 9/1977 | United Kingdom . |

Primary Examiner—Paul R. Michl
Assistant Examiner—Olga Asinovsky

[57] ABSTRACT

An improved process for the production of linear block copolymers of vinylaromatic hydrocarbon and conjugated alkadiene comprises the coupling of living polymer chains containing at least one block of polymerized vinylaromatic hydrocarbon and at least one block of polymerized conjugated alkadiene wherein the coupling agent is an aromatic phosphonite.

17 Claims, No Drawings

POLYMER PROCESS

FIELD OF THE INVENTION

This invention relates to an improved process for the production of linear block copolymers by the coupling of living polymer chains. More particularly, the process relates to an improved process for the production of linear block copolymers of vinyl aromatic hydrocarbon compound and conjugatable alkadiene, which process employs a particular class of coupling agents to couple living polymer chains containing at least one polymerized vinylaromatic hydrocarbon and at least one polymerized conjugated alkadiene.

BACKGROUND OF THE INVENTION

The production of block hydrocarbon copolymers incorporating at least one block of predominately polymerized vinylaromatic hydrocarbon compound, e.g., styrene, and at least one block of predominately polymerized conjugated alkadiene, e.g., butadiene or isoprene, is well-known in the art. The block copolymer products are also well-known and a number are commercial, being marketed by Shell Chemical Company as KRATON® Thermoplastic Rubber. Although the block copolymers are prepared in a variety of geometric types, e.g. linear, branched, radial or star, many of the more useful block copolymers are linear.

In one modification, the linear polymers are produced by a sequential polymerization. A three-block or triblock polymer is illustratively produced by polymerizing a block of vinylaromatic hydrocarbon (conventionally termed an A block) in the presence of a polymerization initiator, typically an alkyllithium. A conjugated alkadiene is subsequently provided to the polymerization mixture without deactivation of the reactive vinylaromatic hydrocarbon polymer chain. Upon completion of the alkadiene polymerization to form a poly alkadiene block (conventionally termed a B block), vinylaromatic hydrocarbon is again provided. Polymerization of the vinylaromatic hydrocarbon produces a third block. The lithium-terminated active or "living" polymer chain is then deactivated and the polymer is recovered by known methods. This type of polymer is conventionally known as an ABA polymer or, if styrene and butadiene are the monomers, as an SBS polymer.

It is also well-known and conventional to produce linear block copolymers by the coupling of the living polymer chains. In such instances, smaller living chains are produced by sequential polymerization and then coupled through the use of a coupling agent. For example, a block of polymerized vinylaromatic hydrocarbon in prepared in the presence of an initiator and conjugated alkadiene is added to produce a polyalkadiene block. The living polymer chains so produced are then coupled. The production of linear block copolymers is often achieved by coupling procedures when polymer of high molecular weight is desired or when it is desired that the end blocks have the same chemical composition and substantially the same molecular weight. To prepare these types of linear block copolymers, the use of sequential polymerization is technically or economically unattractive.

A number of coupling agents to be use in the production of linear block copolymers are well-known, including silicon or tin compounds, aromatic diisocyanates, ester, dialdehydes and diketones. However, certain of these coupling agents, particularly the silicon or tin agents, contain halogen which results in the presence of alkali halides, particularly lithium halide, in the coupled product. Such halides are corrosive and frequently lead to corrosion problems in the processing of the polymer product. Other coupling agents, e.g., the diisocyanates, are toxic. Ester-coupled products frequently lack thermal stability and dialdehydes and diketones have relatively low coupling efficiency.

It is also known to employ a polyfunctional coupling agent but to adjust the relative quantities of coupling agent and living polymer chain to encourage the production of linear coupled polymer product. However, such polyfunctional agents lead to a mixture of coupled products including linear, branched and non-coupled products. For example, the use of trialkylphosphites as disclosed by Kahle et al., U.S. Pat. No. 3,803,266, leads to products other than linear block copolymer. It would be of advantage to provide an improved coupling process for the production of linear block copolymers of vinylaromatic hydrocarbon and conjugated alkadiene wherein the use of coupling agent provides a relatively high coupling efficiency and selectivity to linear block copolymers.

SUMMARY OF THE INVENTION

The present invention provides an improved process for the production of linear block copolymers of vinylaromatic hydrocarbon and conjugated alkadiene. More particularly, the invention provides an improved process for the production of such block copolymers by the coupling of living polymer chains which employs an aromatic phosphonite of defined structure.

DESCRIPTION OF THE INVENTION

The production of linear block copolymers of vinylaromatic hydrocarbon and conjugated alkadiene by sequential and coupling procedures is broadly well-known in the art, as are methods of controlling the molecular weight of the blocks and the configuration of a polymerized alkadiene block. The vinylaromatic hydrocarbon monomer of such block copolymers is styrene or hydrocarbyl-substituted styrene of up to 18 carbon atoms inclusive such as styrene, p-methylstyrene, p-ethylstyrene, p-octylstyrene, m-isopropylstyrene, α-methylsytrene and α,4-dimethylstyrene. Of the vinylaromatic hydrocarbons, styrene and α-methylstyrene are preferred, especially styrene.

The conjuqated alkadiene monomer is 1,3-butadiene (butadiene) or a hydrocarbyl-substituted butadiene of up to 8 carbon atoms inclusive such as 2-methyl-1,3-butadiene isoprene), 1,3-pentadiene, 2,4-dimethyl-1,3-butadiene, 2-methyl-1,3-hexadiene and 1,3-octadiene. The preferred conjugated alkadienes are butadiene and isoprene.

The production of the living polymer chains which are coupled according to the process of the invention are produced in the presence of a polymerization initiator which is typically a hydrocarbyl lithium compound wherein the hydrocarbyl moiety is alkyl or aryl of from 4 to 10 carbon atoms inclusive. The preferred polymerization initiators are alkyllithium compounds and particularly preferred is sec-butyllithium. The amount of initiator to be employed is that amount conventional for the production of block copolymers. Amounts of initiator from about 0.005 mol to about 1.0 mol per mol of monomer undergoing polymerization are typical.

This production of the polymer chains is by sequential polymerization of at least one block of polymerized vinylaromatic hydrocarbon and at least one block of polymerized conjugated alkadiene. By way of example, a block of vinylaromatic hydrocarbon is produced by polymerization in the presence of an alkyllithium polymerization initiator. The resulting product is a lithium-capped polymer of the vinylaromatic hydrocarbon. By virtue of the lithium cap, the polymer chain is "active", i.e., reactive towards further polymerization, or alternatively is termed "living". To the active polymerized vinylaromatic hydrocarbon chain is provided conjugated alkadiene. The resulting polymerization produces a polymer chain of a block of polymerized vinylaromatic hydrocarbon attached to a block of polymerized conjugated alkadiene which incorporates a lithium cap. It is this type of living polymer chain which is coupled according to the present invention.

It should be understood that the order of monomer addition, although determinative of the nature of the final coupled polymer, is not critical to the operation of the present process, so long as the polymer chain contains at least one block of polymerized vinylaromatic hydrocarbon and at least on block of polymerized conjugated alkadiene. A block of conjugated alkadiene could be initially produced, on which is grown a block of polymerized vinylaromatic hydrocarbon. The resulting living polymer chain is then coupled to produce what is conventionally termed a BAB polymer. If styrene and butadiene are chosen as the reacting monomers, the final polymer would also be conventionally known as a BSB polymer. It should also be appreciated that the polymer chain to be coupled is suitably produced by sequential polymerization of more than two blocks. For example, a living polymer chain is suitably produced by sequential polymerization of one block of vinylaromatic hydrocarbon, followed by a block of polymerized conjugated alkadiene and then a second block of polymerized vinylaromatic hydrocarbon. Coupling of the resulting polymer chain produces what is conventionally termed an ABABA polymer.

The polymerization to produce the living polymer chains for coupling is conducted under polymerization conditions in the presence of the polymerization initiator, a hydrocarbon diluent and optionally, a structure modifier. The precise nature of the hydrocarbon diluent is not material and a hydrocarbon which is aliphatic, including cycloaliphatic, or aromatic of from 4 to 10 carbon atoms inclusive is satisfactory. Illustrative hydrocarbon polymerization diluents includes n-pentane, isopentane, n-hexane, cyclopentane, cyclohexane, 2,2,4-trimethylpentane, benzene, toluene and xylene. The cycloaliphatic hydrocarbons are preferred polymerization diluents and particularly preferred is cyclohexane. The diluent is usually employed in excess over the amount of monomer. Amounts of diluent from about 400 parts by weight to about 1500 parts by weight per 100 parts by weight of monomer are satisfactory. In the case of polymerization of conjugated alkadiene, two modes of polymerization are possible. Such polymerization types are known as 1,2 and 1,4 polymerization and the relative proportions of each are in part determined by the presence or absence of a structure modifier, e.g., an ether or a tertiary amine. The nature of these polymerization types and the control of the proportion of each type are well-known and understood in the art.

The polymerization to form the chain to be coupled is conducted under polymerization conditions conventionally employed for the production of block copolymers of vinylaromatic hydrocarbon and conjugated alkadiene. The polymerization temperature is suitably from about −20° C. to about 150° C. although temperatures from about 30° C. to about 90° C. are more often used. The polymerization pressure is sufficient to maintain the reaction mixture in the liquid phase. Such pressures are typically from about 0.8 atm to about 10 atm. Ambient pressure is often employed. The time for polymerization to be complete will depend in part on the quantity of monomer provided. However, typical reaction times are from about 5 minutes to about 6 hours. More frequently, reaction time from about 10 minutes to about 6 hours are satisfactory.

The coupling process of the present invention comprises reaction of the living polymer chains produced as above described with a phosphonite coupling agent in the absence of any material which might terminate the polymer chains or displace the alkali metal from the polymer chain. The phosphonite coupling agent used in the process of the invention is a compound of the formula

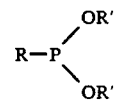

wherein R is a hydrocarbyl aromatic group of up to 10 carbon atoms inclusive and R' independently is a substituted or unsubstituted hydrocarbyl group of up to 10 carbon atoms inclusive which is aliphatic, including cycloaliphatic, or aromatic.

Illustrative R groups include phenyl, tolyl, xylyl, and naphthyl. Hydrocarbyl aliphatic R' groups include methyl, ethyl, 1-methylbutyl, 2-ethylhexyl, cyclopentyl and cyclohexyl. Substituted-hydrocarbyl aliphatic R' groups are those aromatic groups having non-hydrocarbyl groups free from active hydrogen such as methoxybutyl, 2-chloroethyl and 8-ethyloxyoctyl. Aromatic R' groups include hydrocarbyl groups such as phenyl, tolyl or naphthyl and substituted-hydrocarbyl aromatic R' groups are aromatic groups having non-hydrocarbyl substituents free from active hydrogen such as 3-chlorophenyl, 4-methoxyphenyl and 2,4-dimethoxyphenyl.

Illustrative of suitable phosphonite coupling agents are dimethylphenylphosphonite, dibutyltolylphosphonite, diethylphenylphosphonite, dicyclohexylphenylphosphonite, diphenylphenylphosphonite, di(4-methoxyphenyl)phenylphosphonite and di(3-chlorophenyl)-phenylphosphonite. The preferred R group is phenyl and the preferred R' groups are aromatic, preferably phenyl. Particularly preferred as the coupling agent is diphenylphenylphosphonite.

The phosphonite coupling agents are broadly old, although di(3-chlorophenyl)-phenylphosphonite and di(4-methoxyphenyl)-phenylphosphonite are believed novel. The phosphonites are produced by known methods as by heating a dihalophosphine with a slight molar excess of a hydroxy compound in an inert reaction environment. By way of specific example, dichlorophenylphosphine is reacted with 3-chlorophenol under argon to produce di(3-chlorophenyl)-phenylphosphonite.

The coupling process takes place by contacting the living polymer chains and the coupling agent under conditions of temperature and pressure substantially the same as those for polymerization of the polymer chains. The presence of this hydrocarbon reaction diluent is also helpful. The quantities of coupling agent to be used will depend in part upon the proportion of polymerization initiator used to produce the polymer chains. The coupling agent is suitably used in a quantity from about 0.3 mol to about 0.7 mol per mol of polymerization initiator. Quantities of coupling agent from about 0.4 mol to about 0.6 mol per mole of initiator are preferred and especially preferred are quantities of coupling agent from about 0.45 mol to about 0.55 mol per mole of initiator. Subsequent to the coupling reaction, the polymer product of higher molecular weight is obtained by methods conventional for the recovery of such block copolymers, coagulation by steam.

The process of this invention is characterized by a higher coupling efficiency and a higher selectivity to linear product as compared with similar processes using other coupling agents. As used herein, coupling efficiency is defined as the percentage by weight of coupled efficiency is defined as the percentage by weight of coupled polymer based on total polymer and is determined by the percentages of the polymeric species determined by gel permeation chromatography, calibrated against polystyrenes of similar molecular weight. The selectivity to linear coupled polymer is expressed as the percentage of linear coupled polymer based on the total coupled polymer. The process of the invention is particularly applicable to the production of linear block copolymers of relatively high molecular weight or the production of linear block copolymers whose end blocks are desirably substantially the same molecular weight. The coupling agent is present as only a very small percentage of the total polymer and has no substantial effect on the properties of the block copolymer.

The invention is further illustrated by the following Comparative Example (not of the invention) and the following Illustrative Embodiments which should not be regarded as limiting.

ILLUSTRATIVE EMBODIMENT I

In a 500 ml round-bottom three-necked flask equipped with an argon inlet, a Liebig condenser and a magnetic stirrer, a mixture of 11.8 g dichlorophenylphosphine and 23.8 g of freshly distilled 4-methyoxyphenol was heated slowly to 180° C.–200° C. and maintained at this temperature overnight. The hydrogen chloride which formed was allowed to escape through a vent. The conversion of the reacting mixture was followed by $-$P-NMR and after the conversion from phosphine to phosphonite was complete, the residue was distilled in vacuo. The yield of product, B.p. 200° C./0.3 mmHg, was 92% and the NMR spectra were consistent with the compound di(4-methoxyphenyl-phenyl)phosphonite.

ILLUSTRATIVE EXAMPLE II

The procedure of Illustrative Embodiment I was repeated except that the 4-methoxyphenol was replaced with 22.2 g of 3-chlorophenol and 11.5 g of dichlorophenylphosphine was employed. The yield of product, B.p. 168° C./0.001 mmHg, was 77% and the NMR spectra were consistent with di(3-chlorophenyl)phenyl-phosphonite.

ILLUSTRATIVE EMBODIMENT III

Three phenylphosphonites of the invention were evaluated as coupling agents in a coupling process representative of the process of the invention. Into a 500 ml glass bottle equipped with a serum cap were introduced 200 ml cyclohexane, 32 g 1,3-butadiene and 0.63 mmol sec-butyllithium. After mixing, the contents of the bottle were heated to 60° C. in a water bath and maintained at that temperature until polymerization was complete in about 2 hours. Subsequently, 0.252 mmol of the candidate coupling agent was added and the heating was continued for an additional 0.5 hour. The results of the evaluations are shown in Table I were the coupling efficiency was determined by GPC analysis.

TABLE I

| Coupling Agent | Coupling Efficiency, % |
| --- | --- |
| Diethylphenylphosphonite | 47 |
| Dinonylphenylphosphonite | 43 |
| Diisopropylphenylphosphonite | 45 |
| Diphenylphenylphosphonite | 46 |
| Diphenylphenylphosphonite | 64 |

COMPARATIVE EXAMPLE

The procedure of Illustrative Embodiment III was used to evaluate phosphonites not of the invention. In these evaluations, 26 g of 1,3-butadiene and 1.05 mmol sec-butyllithium were used. The results are shown in Table II.

TABLE II

| Coupling Agent | Coupling Efficiency, % |
| --- | --- |
| Dimethylethylphosphonite | 0 |
| Diethylethylphosphonite | 30* |
| Dibutylbutylphosphonite | 17 |

*Product contained 50% branched material

ILLUSTRATIVE EMBODIMENT IV

A 10 liter stainless steel reactor was charged with 6 liters of cyclohexane and 333 g of styrene the mixture was heated to 60° C. The polymerization was initiated by the addition of 25 mmol sec-butyllithium and the heating continued for about i hour until polymerization had been completed. Over a 5 minute period, 667 g of 1,3-butadiene were gradually added and the heating was continued for an additional 2 hours to achieve complete conversion of the butadiene. After the temperature of the mixture had been raised to 80° C., 13 mmol of diethylphenylphosphonite were added. The coupling reaction took place over a 5 hour period. The polymer was isolated by steam coagulation and dried in an oven at 50° C. Based on GPC analysis, the coupling efficiency was 64% with a selectivity to linear product of 100%.

ILLUSTRATIVE EMBODIMENT V

A 10 liter reactor was charged with 7 liters of cyclohexane and 75 g of styrene and the resulting mixture was heated to 50° C. The polymerization was initiated by the addition of 7.2 mmol sec-butyllithium and the polymerization continued at 60° C. until complete in about 30 minutes. Then, 1 ml of 1,2-diethoxyethane was added as a structural modifier to produce polymer having a high 1,2-vinyl content upon addition of 425 g isoprene over 5 minutes. The polymerization continued at 60° C. for one hour until all the isoprene had reacted. Diphenylphenylphosphonite, 3.6 mmol, was then added at 60° C. while the mixture was stirred and the coupling reaction continued for 15 minutes. The resulting mixture was stabilized with 2,6-di-t-butylcresol and the polymer was isolated by steam coagulation and dried in an oven at 50° C. The results are shown in Table III.

ILLUSTRATIVE EMBODIMENT VI

The procedure of Illustrative Embodiment V was repeated except that no structure modifier was added and the coupling was conducted at 70° C. The results are shown in Table III.

ILLUSTRATIVE EMBODIMENT VII

The procedure of Illustrative Embodiment V was repeated except the coupling took place at 80° with di(4-methoxyphenyl) phenylphosphonite as a coupling agent. The results are shown in Table III.

ILLUSTRATIVE EMBODIMENT VIII

The procedure of Illustrative Embodiment V was repeated except that 1,3-butadiene was used instead of isoprene, no structure modifier was used and the coupling was performed at 70° C. The results are shown in Table III.

ILLUSTRATIVE EMBODIMENT IX

The procedure of Illustrative Embodiment V was repeated except that 1,3-butadiene was used instead of isoprene and coupling took place at 80° C. The results are shown in Table III.

TABLE III

| Illustrative Embodiment | Coupling Efficiency, % | Selectivity to linear coupled polymer, % |
|---|---|---|
| V | 85 | 96.5 |
| VI | 84 | 95 |
| VII | 82 | 97.5 |
| VIII | 82 | 95 |
| IX | 89 | 95.5 |

What is claimed is:

1. In the process of producing a linear block copolymer of vinylaromatic hydrocarbon and conjugated alkadiene by coupling living block polymer chains containing at least one block of polymerized vinylaromatic hydrocarbon and at least one block of conjugated alkadiene, the improvement of using as the agent for the coupling an aromatic phosphonite.

2. The process of claim wherein the aromatic phosphonite is represented by the formula

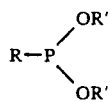

wherein R is hydrocarbyl aromatic of up to 10 carbon atoms inclusive and R, independently is aliphatic or aromatic, free from active hydrogen, of up to 10 carbon atoms inclusive.

3. The process of claim 2 wherein R is phenyl.
4. The process of claim 3 wherein each R' is aromatic.
5. The process of claim 4 wherein R' is phenyl.
6. The process of claim 4 wherein R' is 3-chlorophenyl.
7. The process of claim 4 wherein R' is 4-methoxyphenyl.
8. In the process of producing a linear block copolymer of styrene and butadiene or isoprene by coupling in the presence of a coupling agent living block copolymer chains containing at least one block of polymerized styrene and at least on block of polymerized butadiene or isoprene, the improvement wherein the coupling agent is an aromatic phosphonite.
9. The process of claim 8 wherein the aromatic phosphonite is represented by the formula

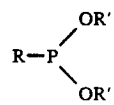

wherein R is hydrocarbyl aromatic of up to 10 carbon atoms inclusive and R' independently is aliphatic or aromatic, free from active hydrogen, of up to 10 carbon atoms inclusive.

10. The process of claim 9 wherein R is phenyl.
11. The process of claim 10 wherein each R' is phenyl.
12. In the process of producing a linear block copolymer of styrene and butadiene by coupling with a coupling agent living block polymer chains containing at least one block of polymerized styrene and at least on block of polymerized butadiene, the improvement of using as the coupling agent an aromatic phosphonite.
13. The process of claim 12 wherein the phosphonite is represented by the formula

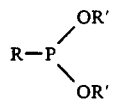

wherein R is phenyl and R' is hydrocarbyl or substituted hydrocarbyl aromatic or aliphatic free from active hydrogen of up to 10 carbon atoms inclusive.

14. The process of claim 13 wherein each R' is aromatic.
15. The process of claim 13 wherein each R' is phenyl.
16. The process of claim 14 wherein each R' is 3-chlorophenyl.
17. The process of claim 14 wherein each R' is 4-methoxyphenyl.

* * * * *